United States Patent [19]

Brumwell et al.

[11] Patent Number: 5,749,910
[45] Date of Patent: May 12, 1998

[54] SHIELD FOR IMPLANTABLE CARDIOVERTER DEFIBRILLATOR

[75] Inventors: Dennis A. Brumwell, Bloomington; Joseph S. Perttu, Chanhassen; Mark W. Kroll, Minnetonka; Randall S. Nelson, Pine Springs, all of Minn.

[73] Assignee: Angeion Corporation, Plymouth, Minn.

[21] Appl. No.: 486,759

[22] Filed: Jun. 7, 1995

[51] Int. Cl.[6] ................................................ A61N 1/375
[52] U.S. Cl. ............................................................. 607/36
[58] Field of Search .............................. 607/36, 37, 38, 607/5; 357/68, 84

[56] References Cited

U.S. PATENT DOCUMENTS

| | | |
|---|---|---|
| 4,774,950 | 10/1988 | Cohen . |
| 4,947,235 | 8/1990 | Roth et al. .................................. 357/68 |
| 5,312,442 | 5/1994 | O'Phelan ...................................... 607/5 |
| 5,370,669 | 12/1994 | Daglow et al. . |
| 5,405,363 | 4/1995 | Kroll et al. . |

*Primary Examiner*—Scott M. Getzow
*Attorney, Agent, or Firm*—Brad Pedersen

[57] ABSTRACT

An implantable cardioverter defibrillator capable of subcutaneous positioning within a patient delivers at least one electrical cardioversion/defibrillation countershocks to the heart of the patient. The implantable cardioverter defibrillator includes a housing, circuitry positioned within the housing to control delivery of the countershocks, and an energy source coupled with the circuitry to provide electrical energy to a capacitor in the circuitry that stores the electrical energy for delivery of the countershocks. Because the circuitry is susceptible to undesirable electromagnetic coupling effects of origin external to the circuitry, particularly the capacitive coupling effects between the circuitry and the housing of the device when at least a portion of the housing is utilized as an electrode, the implantable cardioverter defibrillator also includes a conductive shield, disposed between the housing and the circuitry, to shield the circuitry against such undesired coupling effects.

21 Claims, 7 Drawing Sheets

Fig. 8

SHIELD FOR IMPLANTABLE
CARDIOVERTER DEFIBRILLATOR

1. Field of the Invention

The invention relates to implantable cardioverter defibrillators, and more particularly, to implantable cardioverter defibrillators having internal circuitry subject to adverse capacitive coupling effects.

2. Description of Related Art

Cardiac muscle fibrillation is the rapid and asynchronous contraction of individual muscle fibers in the heart. The result is a slightly quivering and non-functional heart muscle. When fibrillation occurs within the lower chambers of the heart or ventricles, blood flow ceases and, if not corrected within minutes, death of the patient will result. Fibrillation occurring only in the upper chambers of heart or atria results in a diminution of cardiac output that may be symptomatic to the patient. Other forms of cardiac dysrhythmia include ventricular or supraventricular tachycardia, which are very rapid organized/synchronous muscle fiber contractions that impair cardiac output to lesser or greater degrees dependent on cardiac refill times and preload pressures.

Implantable cardioverter and defibrillator (ICD) systems accomplish the desired treatment of cardiac dysrhythmia by passing through the heart muscle a cardioversion or defibrillation countershock, depending on the type of cardiac dysrhythmia diagnosed. An objective of the cardioversion or defibrillation countershock is to immerse as much of the myocardium as possible within the electrical field generated by the countershock. The countershock is a truncated capacitive discharge of electrical energy that generally ranges from 0.1 to 5.0 joules for cardioversion and from 5 to 40 joules for defibrillation of the ventricles.

U.S. Pat. No. 4,774,950, the disclosure of which is incorporated herein by reference, discloses an embodiment of an abdominally implanted ICD. U.S. Pat. No. 5,405,363, the disclosure of which is incorporated herein by reference, describes embodiments of a pectorally implanted ICD.

Conventional abdominally implanted ICDs include a metal housing that floats with respect to the internal electronic circuitry. The housing is not physically secured to the internal electronics and is tied to the battery ground through a high impedance, typically 200K ohms. This is desirable to prevent the housing from acting as an electrode and thereby siphoning off current that should flow between the two defibrillation electrodes. Preventing the housing from acting as an electrode at an abdominal location is especially desirable, to avoid diverting current from the heart. Even though the housing is essentially floating, the housing acts as a shield against electromagnetic interference and protects the internal electronic circuitry from picking up induced pulses from stray electromagnetic fields.

Unlike abdominally implanted ICD's, pectorally implanted ICD's, such as described in U.S. Pat. No. 5,405,363, typically use the housing as one of the electrodes. When the housing is used as an electrode, implanting the housing in the pectoral region on the patient's left side and inserting a transvenous electrode into the patient's right ventricle will cause the defibrillation current to be directed along a very desirable vector. This results in a lower defibrillation threshold, that is, a lower minimum energy to produce successful defibrillation.

A common approach to delivering shocks with an ICD is to divide the shock into more than one phase. With biphasic waveforms, the polarity of the second phase is opposite to that of the first phase. It has been demonstrated that many biphasic waveforms can successfully defibrillate with consistently lower voltage and energy requirements than monophasic waveforms of the same duration. With biphasic waveforms the two electrodes of the defibrillator change polarities in mid-pulse.

When using a pectorally implanted housing as an electrode for biphasic-waveform shocks, the housing must be switched from one polarity of the output capacitor to the opposite polarity. In this case, the housing of the device cannot serve as an electrode simply by tying the housing to one of the battery electrodes, as it could be done for a monophasic pulse. When the housing is configured as an electrode for pectorally implanted ICD delivering a biphasic waveform, the housing acts as a large, first plate of a capacitor, and the other conductors in the circuitry of the ICD act as a second plate of the capacitor. When the housing voltage suddenly changes, voltages and currents are induced on nearby conductors. These induced currents and voltages potentially can be of sufficient magnitude so as to introduce unwanted logic signals or switching signals in the circuitry of the ICD, which have the possibility of causing circuit malfunctions and consequent harm to the patient.

For circuits with conductors having significant length, or lying adjacent to the housing, this kind of induction coupling effect is magnified. Such conductors are common in ICDs having interconnect wiring between various parts of the circuit, for example. These conductors often are in a medium known as a "flex tape," wherein conductive paths are printed on a flexible dielectric film that is wrapped, folded and bent to reach various points of the circuit to which connections must be made. Often, the most convenient route for the flex tape to reach these various points is around the outside of the electronics core, that is, near the inside surface of the housing thereby increasing the likelihood of undesirable induction coupling.

As ICDs become smaller, especially pectorally implanted ICDs, the interconnect conductors and electronics are positioned nearer to the inside housing surface of the device. When the housing of the ICD is used as a switchable electrode, it is no longer possible to couple the housing to ground, for example, to allow the housing to serve as a capacitor coupling shield. Consequently, capacitive coupling problems that have not been experienced in the past are impacting the design and operation of new ICDs. These unanticipated capacitive coupling problems limit the miniaturization and effective operation of such devices.

SUMMARY OF THE INVENTION

To address these and other problems, an ICD according to the invention includes a conductive shield, disposed between the housing and the internal circuitry of the ICD, to shield the circuitry against undesirable coupling effects. The conductive shield is in electrical communication with a reference point, preferably a battery ground or the battery itself, to cause the shielding effect. When the housing of the device acts as a switchable electrode to deliver cardioversion/defibrillation countershocks, the conductive shield shields the internal circuitry from undesirable capacitive coupling effects between the circuitry and the housing of the device. The internal circuitry shielded from such undesirable coupling effects preferably includes an electronic circuit board and/or an interconnect conductor.

Additionally, according to one embodiment, the circuitry that is shielded against the coupling effects preferably includes a flex tape assembly, and the conductive shield preferably is integrated onto the flex tape assembly. One embodiment according to the invention also includes an internal liner in contact with the housing, the conductive shield being supported by and preferably embedded in the liner. The liner preferably includes inner and outer insulative material, the conductive shield being disposed therebetween.

According to another embodiment, a method of delivering electrical cardioversion/defibrillation countershocks according to the invention includes the step of shielding internal circuitry from undesirable coupling effects between the circuitry and an external source. According to a preferred embodiment, the circuitry is shielded from undesirable capacitive coupling effects between the circuitry and the housing, when the housing is used as an electrode for the delivery of countershocks to the patient.

The invention will be described in detail with reference to the following drawings, in which like reference numerals refer to like elements:

DETAILED DESCRIPTION OF PREFERRED EMBODIMENTS

Figure 1:
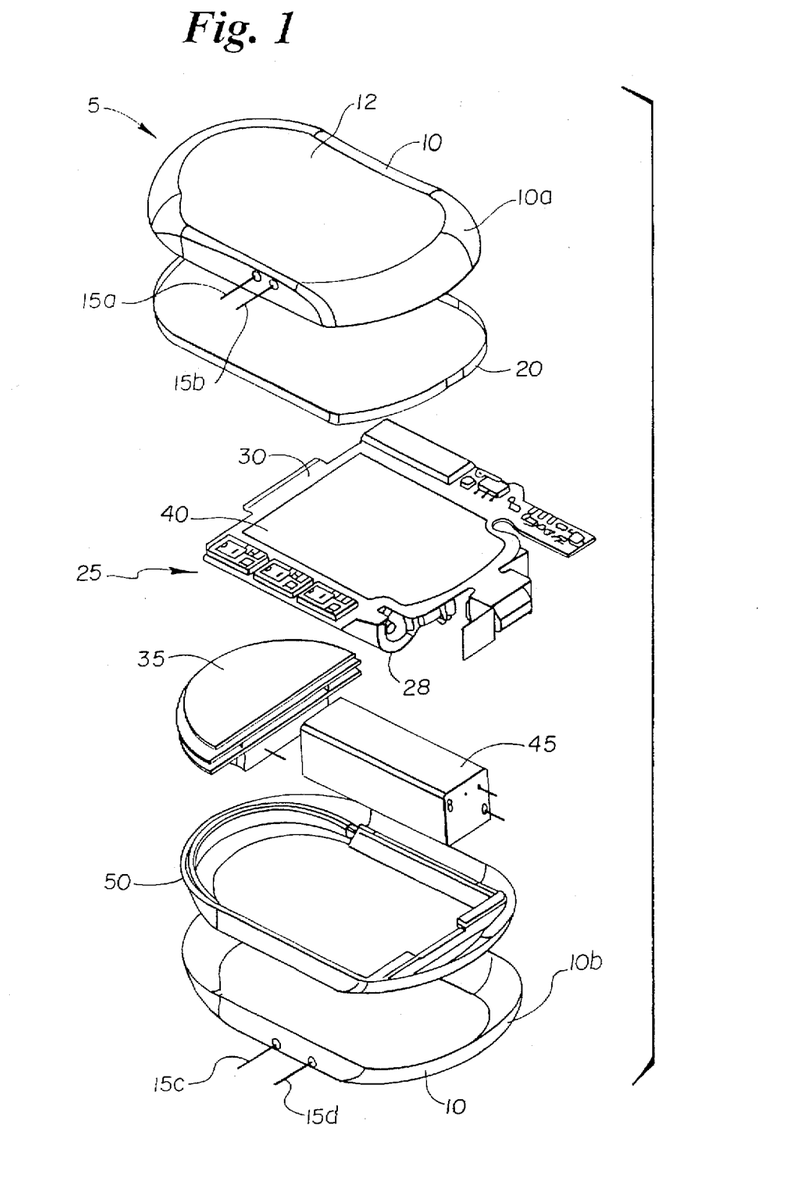
FIG. 1 is a perspective exploded view of an implantable cardioverter/defibrillator according to one embodiment of the invention.

FIG. 1 illustrates an ICD according to a preferred embodiment of the invention. ICD 5 includes a housing preferably formed in two sections 10a, 10b, joined together by a weld ring 20. Of course, single-piece and multi-piece housings having more than two housing sections also are contemplated. Housing 10 preferably is formed of biocompatible material, such as titanium alloy, but also can be formed of other biocompatible metallic or non-metallic conductive materials.

Figure 6:
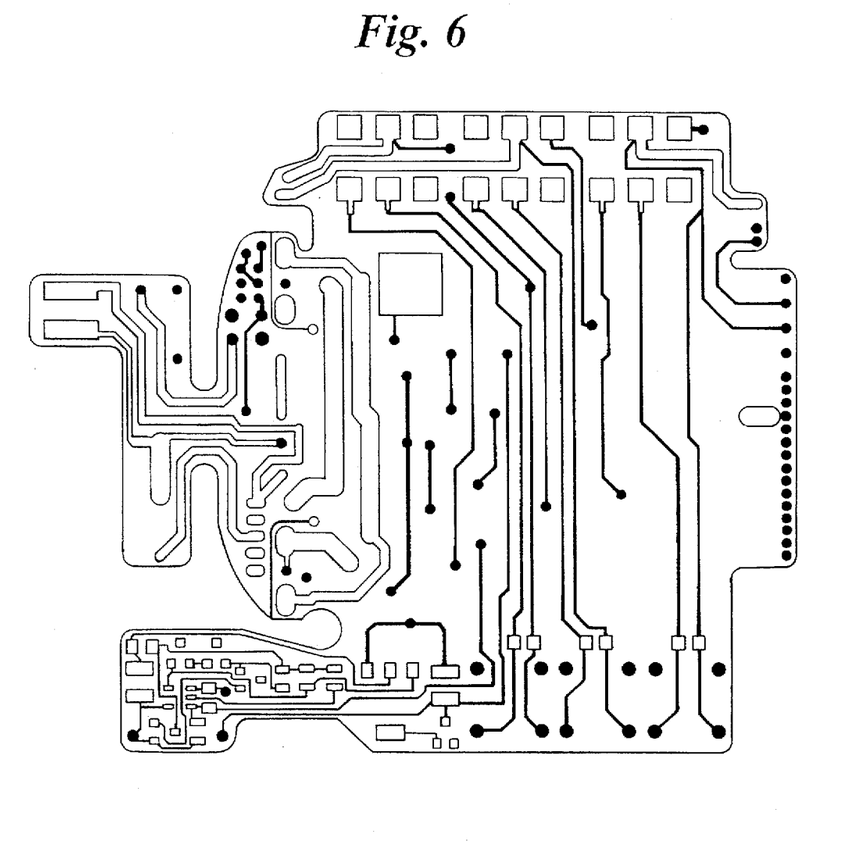
FIG. 6 is a top view of circuitry according to an embodiment of the invention.
Figure 7:
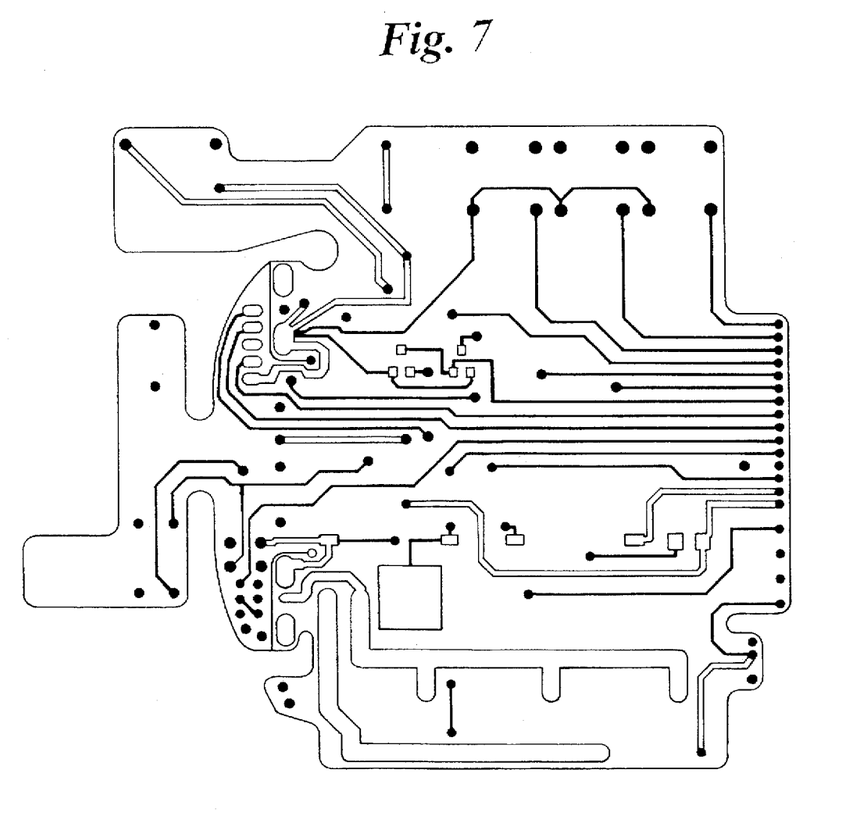
FIG. 7 is a bottom view of circuitry according to an embodiment of the invention.

Positioned within housing 10 is circuitry 25, which controls delivery of countershocks to the myocardium of a patient in a known manner and an embodiment of which is shown in more detail in FIGS. 6–7. Circuitry 25 includes electronic circuit board assembly 35 and flex tape interconnect conductor assembly 30, which are susceptible to undesirable electromagnetic coupling effects of origin external to circuitry 25. Such undesirable coupling effects can include capacitive coupling effects between housing 10 and circuitry 25, for example, when housing 10 is used as an electrode. Additionally, other electromagnetic coupling effects of origin external to the ICD and/or external to the patient can induce unwanted currents and voltages within circuitry 25, leading to malfunction of the ICD and possible consequent harm to the patient.

Circuitry 25 includes at least one capacitor 28 for storing electrical energy to generate the cardioversion/defibrillation countershocks applied to the myocardium of the patient. Although only one such capacitor 28 is shown in FIG. 1, two or more such capacitors also are contemplated by the invention. Of course, a wide variety of different types of capacitors can be used with the ICD according to the invention, including double layer, electrolytic, and electrostatic capacitors. Double layer capacitors have no permanent dielectric, electrolytic capacitors have a permanent dielectric formed on the surface of a metal electrode, while the opposing electrode is an electrolyte, and electrostatic capacitors have a permanent dielectric and two metallic electroplates. Any type of capacitor capable of storing electrical energy to generate the cardioversion/defibrillation countershocks to be applied can be used, according to the invention.

Housing 10 preferably includes plastic insulator 50, which serves to prevent undesired electrical communication between housing 10 and circuitry 25. Further, feedthroughs 15a–15d extend transversely to the surface of housing 10 to provide electrical connection between ICD 5 and a plurality of leads, such as high-voltage electrodes, and pacing and sensing electrodes for the atrium and ventricle, for example, which are unmarked, through a connector port housing (not shown). Other feedthrough arrangements also are contemplated according to the invention. For example, a single multipolar feedthrough can be used instead of a plurality of feedthroughs.

Also disposed within housing 10 is an energy source 45, which is coupled with circuitry 25. Energy source 45 preferably is a battery for providing electrical energy to circuitry 25 for the delivery of countershocks to the myocardium of the patient. Of course, a wide variety of energy sources 45 can be used according to the invention. Such energy sources include lithium/vanadium oxide batteries, as well as lithium/silver vanadium oxide, solid cathode, liquid organic electrolyte batteries, and other batteries capable of operating at low current drains for long periods of time, and capable of then providing high-current pulses when defibrillation is required. Typically, the high-current pulses are in excess of two amperes at voltages above two volts, for periods of as long as ten seconds. The battery cell used, therefore, preferably exhibits high energy density, high current-delivery capability, and low self-discharge. The battery also should meet the applicable safety and reliability standards required of all implantable power sources and have a discharge curve providing a state of charge indication that can signal the need for replacement of the device. Additionally, more than one battery or more than one battery chemistry may be used.

In addition to energy source 45 and one or more capacitors 28, circuitry 25 preferably includes a power transformer to step up the voltage of energy source 45 to a higher voltage for storage on capacitor 28, and also includes at least one switch and diode, as is well known in the art. This high-voltage output circuitry transfers energy stored in the high-voltage capacitor(s) to the heart. The circuitry should perform this transfer function with minimal wasted energy, because implantable batteries and capacitors have limited energy capacity. In addition to the high voltage output circuitry, appropriate sensing and control circuitry are also included in circuitry 25.

To shield circuitry 25 against the undesirable coupling effects to which it is susceptible, ICD 5 includes conductive shield 40, disposed between housing 10 and circuitry 25. Conductive shield 40 preferably is metallic and can be integrated directly onto flex tape interconnect assembly 30, so that the conductor paths of flex tape interconnect assembly 30 lie underneath shield 40. Shield 40 thus shields flex tape interconnect assembly 30 against undesirable coupling effects between assembly 30 and objects external to assembly 30, such as housing 10 when housing 10 is used as an electrode. Of course, shield 40 also shields electronic circuit board assembly 35 against undesirable coupling effects as well.

Figure 8:
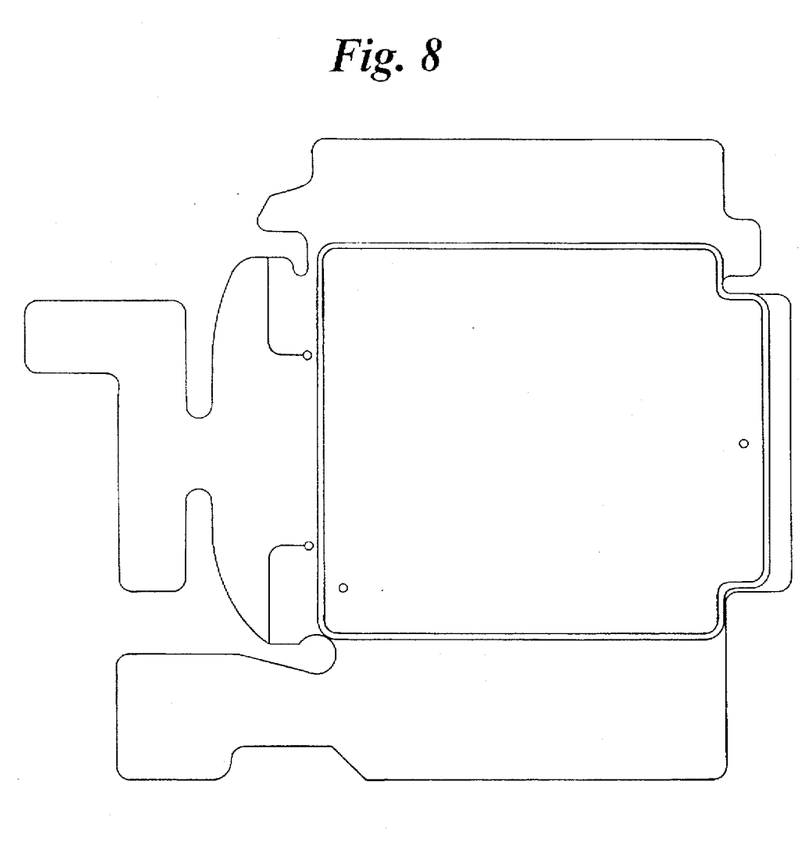
FIG. 8 is a plan view of a shield covering circuitry according to an embodiment of the invention.

Shield 40 need not be integrated onto assembly 30, but can be separated from assembly 30 by an intervening adhesive or other layer, or spaced from interconnect assembly 30 entirely. Additionally, shield 40 need not cover the entire length and width of circuitry 25; shield 40 can cover and thus shield only those portions of circuitry 25 that are susceptible or most susceptible to external coupling effects. One type of shielding arrangement is shown in FIG. 8. Shield 40 is preferably included on only one side of ICD 5 which, when implanted, faces the myocardium and which may include a mesh electrode surface 12 on a portion of housing 10. Alternatively, circuitry 25 could be disposed between a pair of shield 40 positioned on each side of ICD 5.

Figure 2:
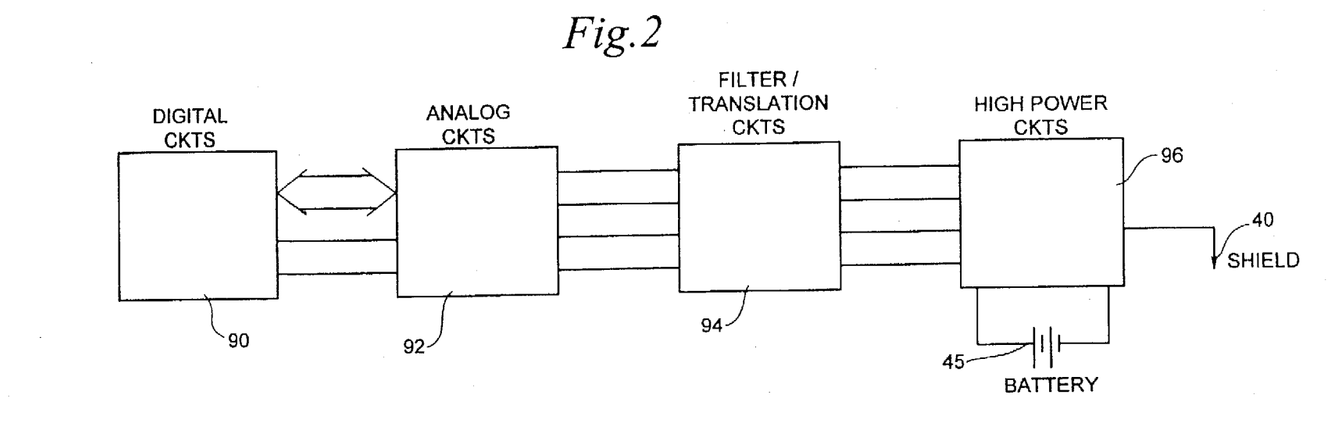
FIG. 2 is a circuit diagram showing elements of the FIG. 1 defibrillator.
Figure 3:
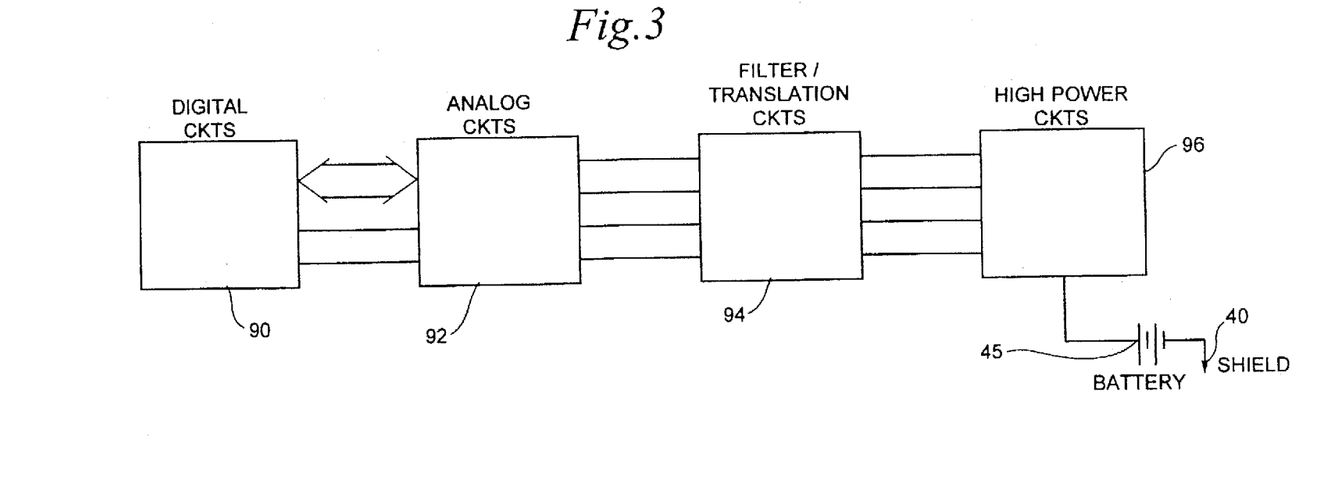
FIG. 3 is a circuit diagram showing elements of the FIG. 1 defibrillator according to an alternative embodiment.

FIGS. 2–3 are circuit diagrams showing elements of the FIG. 1 defibrillator. Digital circuitry 110, analog circuitry 115, filter/translation circuitry 120 and high power circuitry 125 are in electrical communication as shown in FIGS. 2–3. Conductive shield 40 is in electrical communication with a reference point, which now will be further described. According to the FIG. 2 embodiment, the reference point is a battery ground, that is, shield 40 is indirectly connected to the ground plane through high power circuitry 120. According to the FIG. 3 embodiment, the reference point is on battery 45 itself, preferably on the high side of the battery. Connecting shield 40 to the reference point enables conductive shield 40 to shield circuitry 25 against the previously described undesirable coupling effects by acting as a ground plane for undesired electromagnetic radiation. Of course, the reference point also can be disposed at other points, such as any point in the circuit that passes high frequency current efficiently to the average circuit potential. This includes capacitive or direct connections to the defibrillator battery or even the high voltage capacitors. Note the discussion below with respect to FIG. 5.

Figure 4:
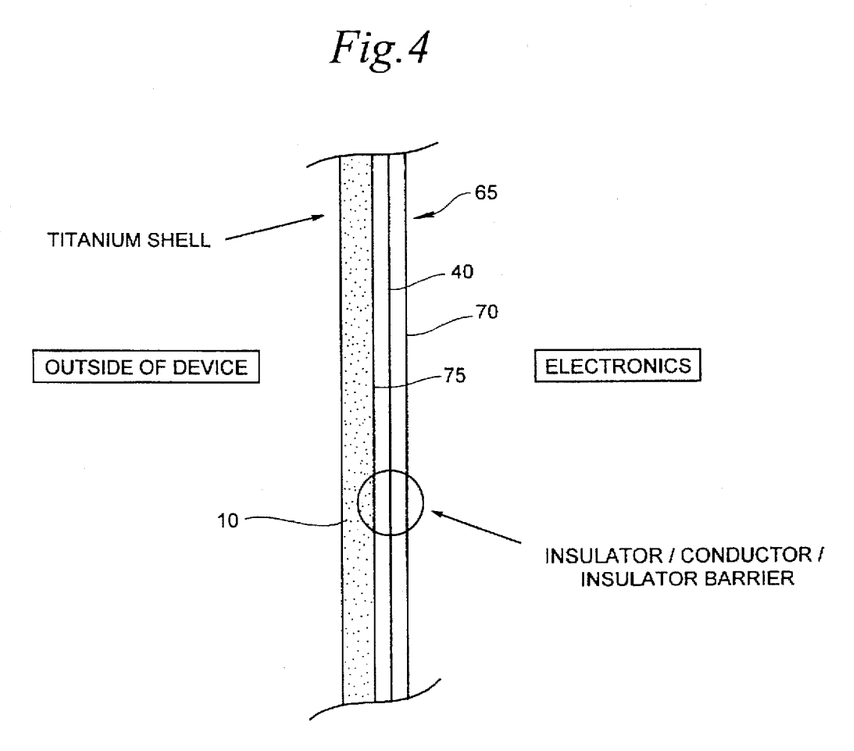
FIG. 4 is a cross-sectional view of an ICD housing and shield according to an alternative embodiment of the invention.

According to the ICD embodiment of FIG. 4, conductive shield 40 is embedded in liner 65, preferably formed of a plastic that covers the entire inner surface of housing 10. According to this embodiment, the entire area inside housing 10 is shielded from capacitive coupling effects due to housing 10, and from electromagnetic coupling effects of origin external to ICD 5. Plastic liner 65 preferably includes inner insulative material 70 and outer insulative material 75, between which conductive shield 40 is disposed. As with previous embodiments, conductive shield 40 preferably is electrically connected to the system ground or to some other reference point. Although this embodiment is advantageous in that it shields the entire interior of housing 10, not just circuitry 25, this embodiment requires ICD 5 to be of slightly larger dimensions.

Preferably, the FIG. 4 embodiment according to the invention is of composite, three-ply sandwich insulator-conductor-insulator construction. According to an alternative embodiment, however, liner 65 can be of two-sheet construction, in which one of insulative layers 70, 75 includes a sputtered surface forming conductive shield 40. For example, outer insulative layer 75 can include a sputtered inner surface, or inner insulative layer 70 can include a sputtered outer surface, and inner insulative layer 70 or outer insulative layer 75, respectively, can be formed as a separate layer. The insulator-shield-insulator arrangement preferably is thermoformed into liners 65, as shown in FIG. 4. Upon assembly, liners 65 would overlap and be electrically connected one to the other or through the device circuitry 25.

Insulative layers 70, 75 preferably are formed of a thin (less than 0.010 inch) thermoformable film that is at least moderately tear and puncture resistant and that has a minimum 2,000 volt dielectric strength. Conductive shield 40 can be formed of copper, aluminum or other similar conductive materials, and preferably has a resistance of less than 10 ohms over a 3.5 inch length of sheet 2.5 inches wide. Shield 40 supports 2 amp pulse current at a voltage of 20 volts, according to a preferred embodiment. Shield 40 need not be solid; a fine mesh grid also will perform satisfactorily. For example, the microcracks to be expected by forming a sputtered metal would perform as a grid system. Electrical connection to internal circuitry 25 preferably is through a wire that is soldered, welded, or otherwise attached to a point on the flex circuit. Of course, other suitable connection arrangements also are contemplated by the invention.

Figure 5:
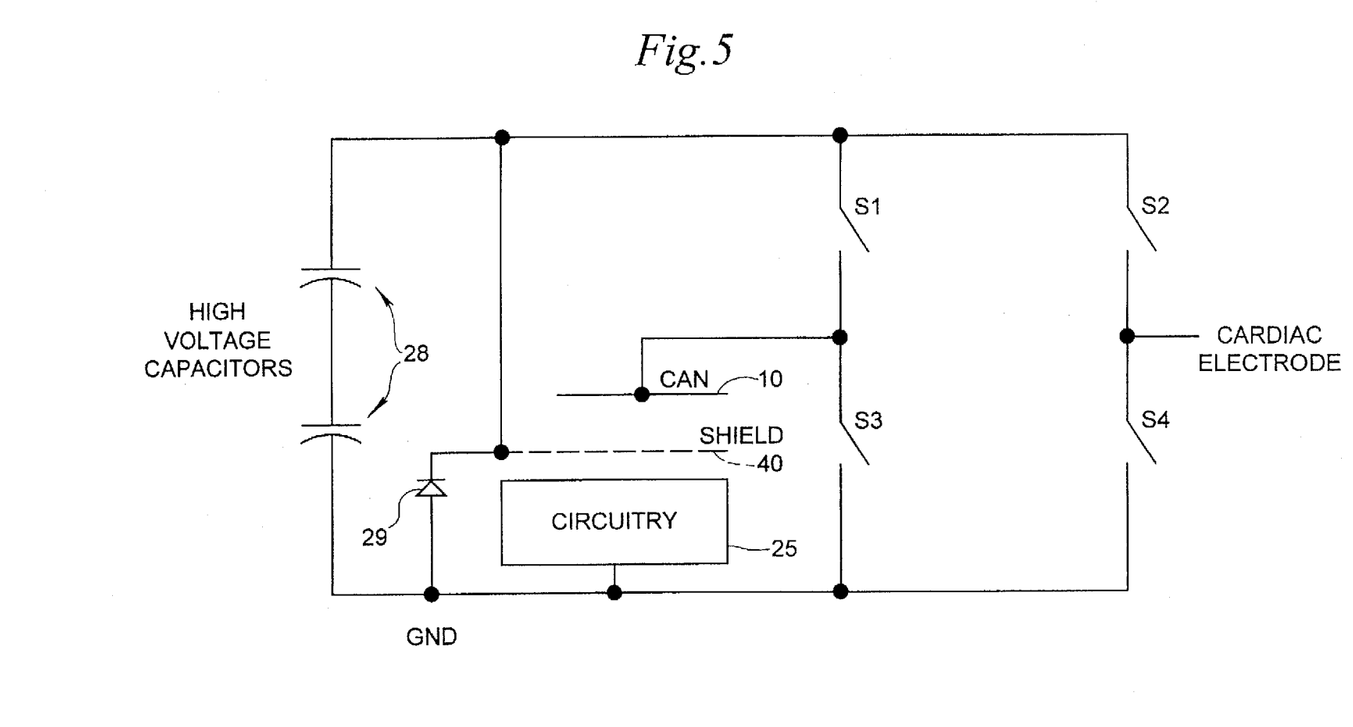
FIG. 5 is a circuit diagram showing an ICD according to an alternative embodiment of the invention.

An alternative embodiment is shown in FIG. 5. An H-bridge switch configuration comprising switches 51–54 is provided, in which one of the two electrodes connected to the H-bridge is housing or can 10. Here shield 40 is electrically connected to the highest voltage, the positive side of energy-storage capacitor(s) 28. This arrangement has several advantages. Capacitor(s) 28 charge up rather slowly, over several seconds, so there is no positive-going spike (dV/dt) to couple capacitively through to circuitry 25. When switch S1 is closed and the housing 10 energized, shield 40 provides a capacitive shunt from housing 10 back to switch S1. Thus, no current flows through circuitry 25.

When the phase of the shock switches, switch S1 is opened and switch S3 is closed. The capacitively coupled current from shield 40 to housing 10 is conducted both through diode 29 and high voltage capacitor(s) 28.

While the invention has been described with reference to specific embodiments, the description is illustrative and is not to be construed as limiting the scope of the invention. Various modifications and changes may occur to those skilled in the art without departing from the spirit and scope of the invention.

What is claimed is:

1. An implantable cardioverter defibrillator capable of subcutaneous positioning within a patient for delivering at least one electrical cardioversion/defibrillation countershocks of at least 0.5 Joules to at least two electrodes adapted to be positioned proximate the heart of the patient, the implantable cardioverter defibrillator comprising:

a housing comprising a biocompatible material;

circuitry positioned within the housing to control delivery of the countershocks, the circuitry being susceptible to undesirable coupling effects of origin external to the circuitry;

an energy source coupled with the circuitry to provide electrical energy to the circuitry;

a conductive shield disposed between the housing and the circuitry to shield the circuitry against the coupling effects; and a reference point in the circuitry, the conductive shield being in electrical connection with the reference point to cause the conductive shield to shield the circuitry from the coupling effects.

2. The implantable cardioverter defibrillator of claim 1, wherein the housing includes at least a portion of the housing which is utilized as an electrode operatively coupled with the circuitry to deliver the cardioversion/defibrillation countershocks, and wherein the conductive shield shields the circuitry from undesirable capacitive coupling effects between the circuitry and the housing when the portion of the housing is utilized as an electrode.

3. The implantable cardioverter defibrillator of claim 1, wherein the circuitry comprises an interconnect conductor.

4. The implantable cardioverter defibrillator of claim 3, wherein the conductive shield shields the interconnect conductor against undesirable coupling effects between the interconnect conductor and external electromagnetic fields.

5. The implantable cardioverter defibrillator of claim 1, wherein the circuitry comprises an electronic circuit board.

6. The implantable cardioverter defibrillator of claim 1, wherein the reference point in electrical communication with the conductive shield comprises a ground.

7. The implantable cardioverter defibrillator of claim 1, wherein the energy source comprises a battery, further wherein the reference point in electrical connection with the conductive shield comprises a point on the battery.

8. The implantable cardioverter defibrillator of claim 1, wherein the circuitry comprises a flex tape assembly.

9. The implantable cardioverter defibrillator of claim 8, wherein the conductive shield is integrated to the flex tape assembly.

10. The implantable cardioverter defibrillator of claim 1, further comprising an internal housing liner in contact with the housing, the conductive shield being supported by the liner.

11. The implantable cardioverter defibrillator of claim 10, wherein the conductive shield is embedded in the liner.

12. The implantable cardioverter defibrillator of claim 10, wherein the liner comprises inner insulative material and outer insulative material, the conductive shield being disposed between the outer insulative material and the inter insulative material.

13. The implantable cardioverter defibrillator of claim 1 wherein the conductive shield comprises two layers of insulating material and the circuitry is operably disposed therebetween.

14. An implantable cardioverter defibrillator capable of subcutaneous positioning within a patient for delivering at least one electrical cardioversion/defibrillation countershocks of at least 0.5 J to at least two electrodes positioned proximate the heart of the patient, the implantable cardioverter defibrillator comprising:

capacitor means for storing electrical energy to generate the cardioversion/defibrillation countershocks;

circuit means for controlling delivery of the cardioversion/defibrillation countershocks to at least two electrodes;

battery means in electrical communication with the capacitor means and circuit means for providing electrical energy to the capacitor means and the circuit means;

housing means comprising a biocompatible material for housing the capacitor means, the circuit means and the battery means, the housing means including an electrode portion forming at least one of the at least two electrodes, the electrode portion of the housing means being in sufficiently close proximity to the circuit means to promote undesirable capacitive coupling effects between the housing means and circuit means; and conductive shielding means disposed between the electrode portion of the housing means and the circuit means for shielding the circuit means against the capacitive coupling effects between the housing means and the circuit means, the conductive shielding means being in electrical communication with a reference point to cause the shielding means to shield the circuit means against the capacitive coupling effects.

15. The implantable cardioverter defibrillator of claim 14, wherein the circuit means comprises an interconnect conductor, further wherein the conductive shielding means shields the interconnect conductor against undesirable coupling effects between the interconnect conductor and an object external to the interconnect conductor.

16. The implantable cardioverter defibrillator of claim 14, wherein the reference point in electrical communication with the conductive shielding means comprises a ground.

17. The implantable cardioverter defibrillator of claim 14, wherein the reference point in electrical communication with the conductive shielding means comprises the battery means.

18. A method of delivering electrical cardioversion/defibrillation countershocks of at least 0.5 J from an implantable cardioverter defibrillator positioned subcutaneously within a patient to at least two electrodes positioned proximate the heart of the patient, the method comprising:

(a) storing electrical energy in at least one capacitor disposed within a housing of the implantable cardioverter defibrillation to generate the cardioversion/defibrillation countershocks;

(b) controlling delivery of the cardioversion/defibrillation countershocks to the at least two electrodes using circuitry disposed within the housing of the implantable cardioverter defibrillator; and (c) using a conductive shield other than the housing to shield the circuitry from undesirable coupling effects between the circuitry and an electromagnetic field external to the circuitry.

19. The method of claim 18, wherein step (c) includes the step of connecting the conductive shield disposed between the circuitry and the housing to a ground.

20. The method of claim 18, wherein the step (c) includes the step of connecting the conductive shield disposed between the circuitry and the housing to the battery.

21. The method of claim 18, wherein the step (c) includes the step of shielding the circuitry from undesirable capacitive coupling effects between the circuitry and the housing when at least a portion of the housing is used as one of the at least two electrodes for delivery of countershocks to the patient.

* * * * *